(12) United States Patent
Furter

(10) Patent No.: US 6,798,506 B2
(45) Date of Patent: Sep. 28, 2004

(54) METHOD AND DEVICE FOR DETECTING IMPURITIES IN A LONGITUDINALLY MOVING THREAD-LIKE PRODUCT

(75) Inventor: Richard Furter, Zug (CH)

(73) Assignee: Uster Technologies AG, Uster (CH)

( * ) Notice: Subject to any disclaimer, the term of this patent is extended or adjusted under 35 U.S.C. 154(b) by 0 days.

(21) Appl. No.: 10/303,751

(22) Filed: Nov. 26, 2002

(65) Prior Publication Data

US 2003/0107729 A1 Jun. 12, 2003

(30) Foreign Application Priority Data

May 31, 2000 (CH) ................................................ 1092/00
May 14, 2001 (WO) ................................ PCT/CH01/00293

(51) Int. Cl.$^7$ ............................................................. G01N 21/00
(52) U.S. Cl. ................................................................... 356/238.2
(58) Field of Search ............................ 356/238.1–283.3; 250/562, 572; 382/141, 143, 111

(56) References Cited

U.S. PATENT DOCUMENTS

| | | | |
|---|---|---|---|
| 4,563,095 A | * | 1/1986 | Puffer ............................ 356/430 |
| 5,054,317 A | | 10/1991 | Laubscher |
| 5,383,017 A | * | 1/1995 | Schurch ...................... 356/238.3 |
| 5,414,520 A | | 5/1995 | Joss et al. |
| 5,832,709 A | | 11/1998 | Lassmann et al. |
| 5,915,279 A | | 6/1999 | Cantrall et al. |
| 5,926,267 A | | 7/1999 | Farber |
| 5,966,211 A | * | 10/1999 | Lilja ............................. 356/238.2 |

FOREIGN PATENT DOCUMENTS

| | | |
|---|---|---|
| EP | 0401600 | 12/1990 |
| EP | 0545129 A1 | 11/1992 |
| EP | 1006225 A2 | 11/1999 |
| WO | WO93/13407 | 7/1993 |

* cited by examiner

Primary Examiner—Michael P. Stafira
(74) Attorney, Agent, or Firm—Burns, Doane, Swecker & Mathis, L.L.P.

(57) ABSTRACT

A first parameter is detected on a fast moving strip or yarn with a wave field, and a first signal indicating potentially present contaminants or impurities is generated. This first parameter preferably detects reflection properties that can be detected on the surface of the product. A further parameter is detected on the strip or yarn in a field, and a second signal is generated which also indicates contaminants or impurities. This second parameter preferably detects properties such as mass or diameter of the yarn or strip. Evaluations of the first signal and the second signal that occur at the same location on the product are considered together, and labeled to indicate the specific type of impurity or contaminant that they represent. Using empirical analysis, evaluation specifications can be selected to identify a group of impurities which are most likely to include a specific impurity of interest, e.g. non-vegetable contaminants.

20 Claims, 6 Drawing Sheets

METHOD AND DEVICE FOR DETECTING IMPURITIES IN A LONGITUDINALLY MOVING THREAD-LIKE PRODUCT

This disclosure is based upon Swiss Application No. 1092/00 filed May 31, 2000, and International Application No. PCT/CH01/00293 filed May 14, 2001, the disclosures of which are incorporated herein by reference.

FIELD OF THE INVENTION

The present invention relates to a method and device for detecting impurities in a longitudinally moving thread-like product made of textile fibers.

BACKGROUND OF THE INVENTION

A method and device for detecting contaminants, in particular foreign fibers in elongate textile structures, are known from U.S. Pat. No. 5,414,520. The structure, for example a yarn, is illuminated with light in a first sensor and the extent of the light reflected by the yarn is measured. As a result, contaminants are detected whose color, structure or surface composition differs from that of the base material of the yarn. However, deviations in the mass or diameter of the yarn can also be detected at the same time. To eliminate these deviations the structure is illuminated from the opposite side in the same or in a different sensor, so the sensor accordingly measures the shadowing owing to the structure. If the signal produced by the reflection and the signal produced by the shadowing are combined, an impurity signal is produced which is independent of the influence of the mass or the diameter of the structure. The cutting blade of a yarn clearer, or the drive of a spinning machine on which the yarn clearer is provided, is conventionally controlled by this impurity signal, to remove detected contaminants.

Every removal of a contaminant results in a cut and subsequent joining of the adjacent portions of a yarn or strip, for example by splicing. If this occurs on a bobbin winding machine, the winding head is stopped. If this occurs on a spinning machine, the relevant spinning point is stopped. This means that removal of the contaminants, for example from textile yarns, during the production process causes losses in the output of the affected machines owing to such stoppages. In particular, in spinning machines these losses consist not only of the periods of time required to separate the yarn and join it again, other stoppage times can be effected if there is an obligatory pause until the joining apparatus, which conventionally has to service many spinning points, is available and has reached the dubious spinning point. Therefore, on one hand it is desirable to remove impurities or contaminants in order to avoid problems during subsequent processing, such as weaving, dyeing or improving. However, it is not desirable for the power of the machines to be impaired thereby.

For these reasons it is desirable, for example, for the manufacturer of a textile intermediate product, such as strip, yarn etc., to be aware of whether and to what extent he wishes to remove contaminants or impurities in the strip or yarn. His possibilities for making a choice are, however, very limited if he only has the opportunity to set a threshold, beyond which a contaminant is removed or not.

It is therefore an object of the present invention to provide a method and a device with which contaminants or impurities can be detected and removed on the basis of substantially differentiated criteria.

SUMMARY OF THE INVENTION

In accordance with the invention, a first parameter is detected on a fast moving strip or yarn with a wave field, and a first signal indicating potentially present contaminants or impurities is generated. This first parameter preferably detects reflection properties that can be detected on the surface of the product. In addition, a further parameter is detected on the strip or yarn in a field, and a second signal is generated which also indicates contaminants or impurities. This second parameter preferably detects properties such as mass or diameter of the yarn or strip, which can be ascertained by measuring the shadowing of a wave field or a change in the capacitance in an electrical field. Therefore a variable, optionally belonging to a group of variables, is determined as a second parameter, this group including the mass and diameter of a portion of the product. Separate evaluation criteria, for example limit values, are allocated to the first signal and the second signal, both signals indicating possible contaminants or impurities. Finally, the evaluations of the first signal and the second signal or parameter that occur at the same location on the product are considered together, and labeled to indicate the specific type of impurity or contaminant that they represent. Thus, the type of impurity is associated with the selected evaluation criteria. Using empirical analysis, evaluation specifications can be selected to identify a group of impurities which are most likely to include a specific impurity of interest, e.g. non-vegetable contaminants.

It is particularly advantageous to ascertain the two parameters in fields which differ greatly owing to their physical properties. Therefore, very different fields can be used, for example light of different wavelengths or light and an electrical field, etc. The two parameters or the signals derived therefrom are observed or detected over a predetermined time, possibly integrated and only after this time compared with the evaluation specifications or measured with respect thereto.

The corresponding device has a first sensor operating with a wave field and a second sensor operating with a field, a processor connected to the first sensor and the second sensor with a memory for time-limited storage of the signals from the first sensor and the second sensor, and software for the processor which presets the evaluation specifications for the first and second signals. A third signal, for selecting impurities likely to include an impurity of interest, is generated from the first signal and the second signal. Light of a specific color is preferably provided for the first sensor as a wave field, and an electrical field for the second sensor.

A device for monitoring parameters of a running thread-like yarn is known from EP 0 401 600. In this device, a capacitively operating sensor and an optically operating sensor arranged adjacent to one another and provide measured values derived from the yarn. The evaluation of the two signals is not, however, made with respect to the detection of contaminants or foreign fibers, but rather with respect to the reduction in the dependence of foreign influences, such as moisture, material influence, dependence on the shape, etc., during measurement of the uniformity or for the promotion of operator-control. There is no disclosure of differentiated detection of contaminants in this publication.

A method and a device are known from GB 2,095,828 which are very similar to those from U.S. Pat. No. 5,414,520. Specifically, the reflection and transmission of light on a fiber entanglement are also measured here. The formation of the relationship of the signals from the reflection and the transmission lead to a signal allowing fibrous and vegetable faults to be distinguished. As a result of further investigations of these signals with respect to details on size, transparency to light and shape, a more precise classification of the faults may be made. This very extensive investigation of faults is, however, intended for non-wovens which are not moved quicker than about 1.5 m/min and which consist of wool, wherein those elements not originating from sheep wool are also to be regarded as contaminants. In contrast, yarns, for example, are moved during spinning at 200 to 400 m/min and during winding at up to 2,500 m/min, so in such cases these complex investigations cannot be carried out in time.

In a strip or yarn, fibers consisting of plastic material, cords, human and animal hairs, feathers etc., are referred to herein as non-vegetable contaminants or impurities, and are particularly disruptive. With cotton as the base material for the yarn, for example, leaf residue, husk portions, seed portions etc. from the cotton, which constitute vegetable contaminants or impurities, are less disruptive. In other words, vegetable contaminants are those elements originating from the cotton plant. Elements or materials not originating from the cotton plant are called non-vegetable. However, these elements can still be natural products, such as hair or feathers.

The advantages achieved by the invention can be seen in that, on one hand, the drawbacks during subsequent processing and, on the other hand, the drawbacks during production of the current intermediate product, such as the yarn or strip, can be avoided owing to a purposefully differentiated classification and elimination of selected impurities in accordance with the aforementioned points of view. As an example, a class of impurities which is most likely to contain non-vegetable impurities can be predetermined when detecting contaminants in the form of an evaluation specification for the signals received. This means, for example, that most or all of the non-vegetable contaminants could be removed, while many vegetable contaminants could be left in the yarn. Such a classification results in the advantage that many contaminants do not have to be cut out of the yarn or strip. These contaminants do not impair subsequent processing, for example dyeing, since the vegetable impurities take up the dye equally as well as the cotton. Alternatively, possible original differences in color might be compensated during bleaching. However, such a classification also results in the advantage that fewer cuts are made in the yarn and therefore the output of the spinning or bobbin winding machine is not reduced so drastically.

BRIEF DESCRIPTION OF THE DRAWINGS

The invention will be described in more detail hereinafter with reference to an example and to the accompanying figures, in which.

DETAILED DESCRIPTION

Figure 1:
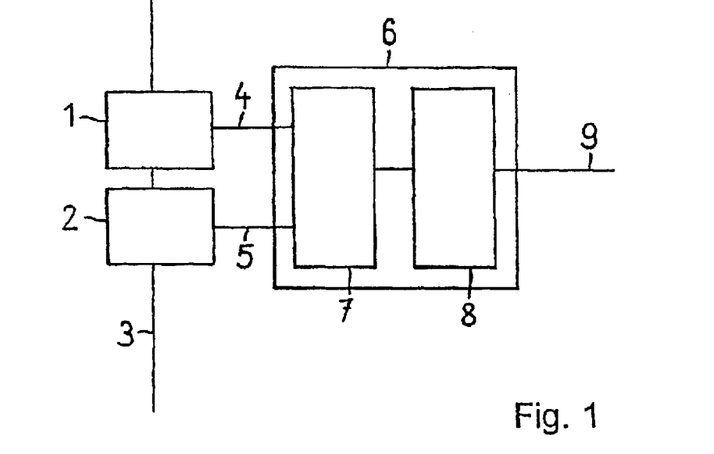
FIG. 1 is a schematic diagram of a device according to the invention.

FIG. 1 shows, schematically, a device according to the invention. It includes a first sensor 1, which can be constructed, for example, as an impurity sensor, as is known from EP 0 761 585. It also includes a second sensor 2 responding specifically to the mass or diameter of the yarn 3. A sensor 2 of this type is known, for example, from U.S. Pat. No. 5,530,368. The sensors 1 and 2 are connected to a processor 6 via connections 4 and 5. The processor has a memory 7, a computer 8 and an output 9 for a differentiated impurity signal. The processor 6 contains software which presets the evaluation specifications for the first and second signals, with which a third signal 9, distinguishing at least two classes of impurity, is generated from the first signal and the second signal.

Figure 2:
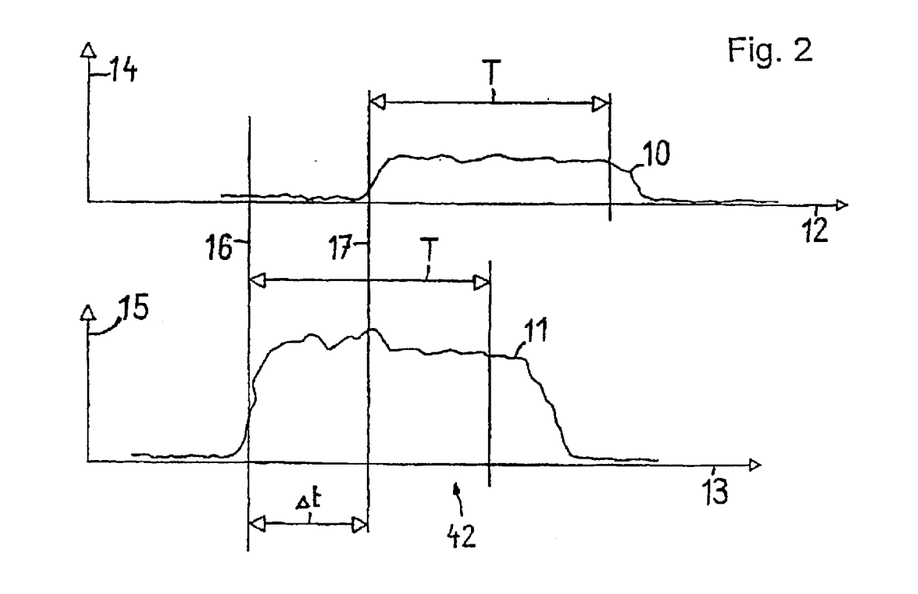
FIG. 2 is a diagram of signals from two sensors of the device in FIG. 1.

FIG. 2 shows a first signal 10 from the first sensor 1 and a second signal 11 from the second sensor 2. Both signals 10 and 11 are plotted over time axes 12 and 13. Values for the reflection of the wave field on the yarn 3 are plotted over the axis 12 along an axis 14 and values for the mass or diameter of the yarn 3 are plotted along an axis 15. Markings 16 and 17 indicate a time difference $\Delta t$ proportional to the spacing of the two sensors 1 and 2 from one another and the speed at which the yarn is moved. T designates a time during which a signal is stored.

Figure 3:
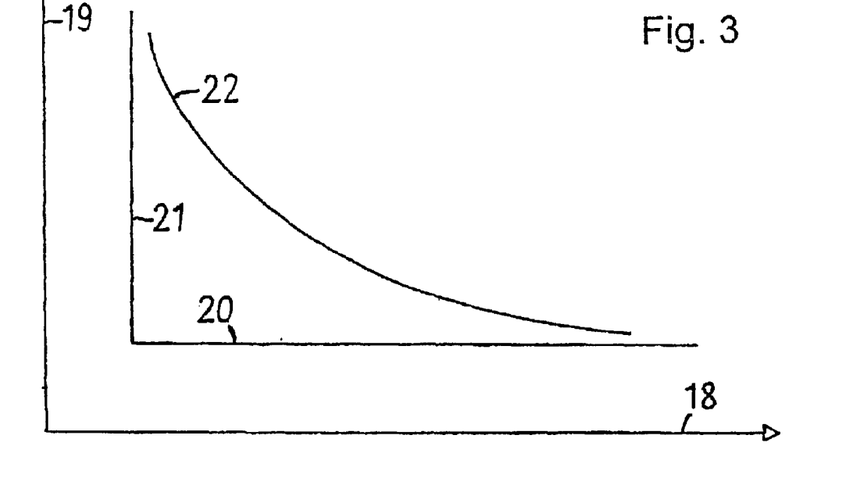
FIG. 3 is a diagram of dimensions of contaminants and of possible limits for signals connected therewith from the sensors.

FIG. 3 shows one known way of organizing yarn faults, irrespective of whether they are connected with contaminants, in accordance with their length or increase in thickness, in that their size is entered into the field extending between axes 18 and 19. Values for the length of a fault are plotted along the axis 18, and values for the extent of the fault, transverse to the longitudinal direction of the yarn, are plotted along the axis 19. The lines 20–21 and 22 indicate two of many possibilities as to how limits can be set in the yarn for faults or contaminants in the yarn or generally. Typically, such contaminants or impurities, which owing to their dimensions come to lie above and to the right of the lines 20–21 or 22, are unacceptable or not desired.

Figure 4:
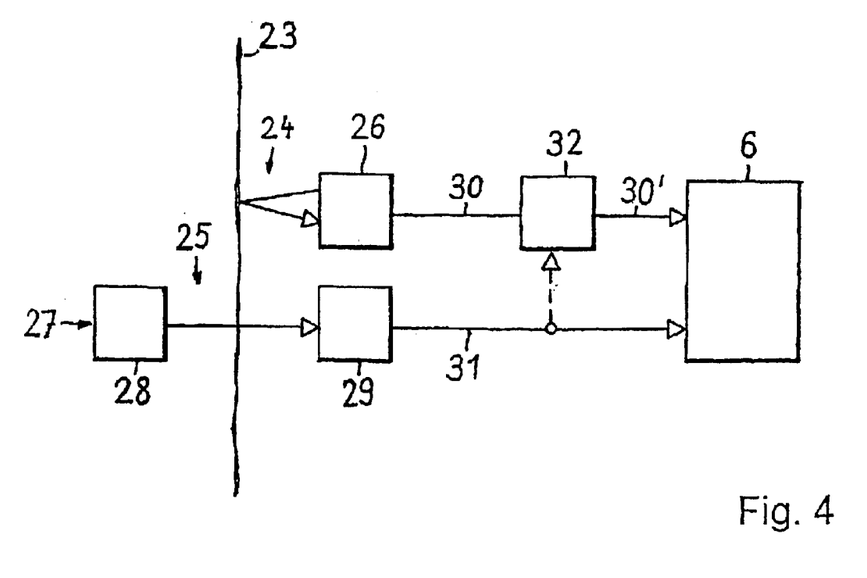
FIG. 4 is a further diagram of a device according to the invention and FIGS. 5, 6, 7 and 8 are each diagrams of possible evaluation criteria.

FIG. 4 shows another embodiment of the device according to the invention, with a strip or yarn 23 crossing a wave field 24 and a further field 25. A first sensor 26 and a second sensor 27 can be seen, the sensor 26 comprising, for example, a transmitter and a receiver for light and the sensor 27 comprising elements 28, 29 which are, for example, designed either as transmitter 28 and receiver 29 for light or as capacitor electrodes 28, 29. The two sensors 26, 27 are connected to a processor 6 via lines 30 and 31. An optionally present element 32 can serve to combine the signals from the lines 30 and 31 in order to generate a corrected impurity signal in the line 30'. This is particularly the case if the sensor 27 is designed for a transmitted light measurement.

Figure 5:
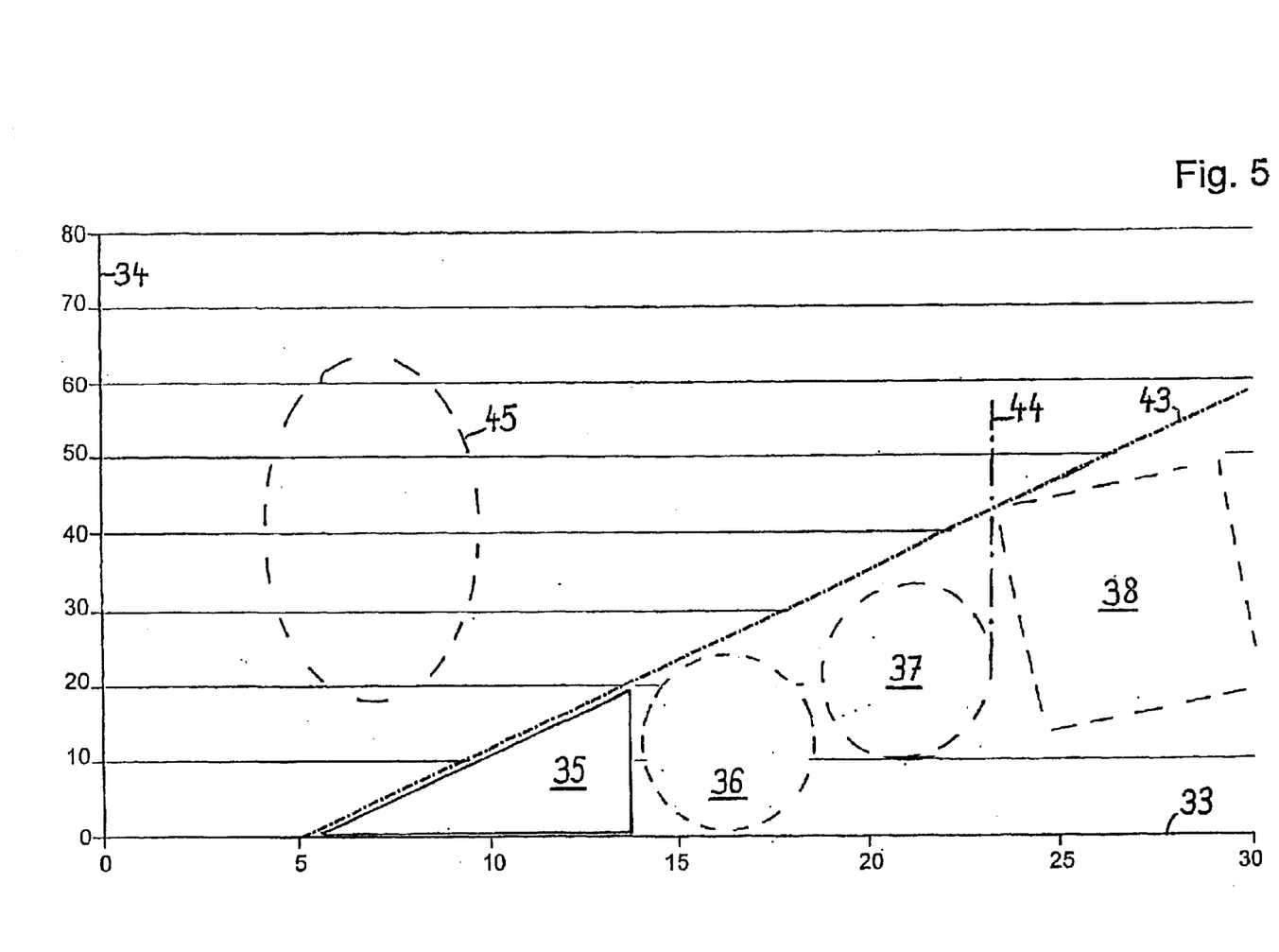

FIG. 5 shows a diagram of evaluation criteria for a classified assessment of impurities or contaminants. For this purpose, values for the signal deviation in a wave field, such as the wave field 24, are plotted along a horizontal axis 33 and signal deviations in a field, such as the field 25, are plotted along a vertical axis 34. The numbers on the axis 33 relate, for example, to values for the reflection of the wave field on the product and the numbers on the axis 34 indicate values for the change in the capacitance in a capacitor or in the transmission of light or waves generally. Here the values 0 represents averages or basic values and the numerical values indicated to the right and upwards are based on percentage deviations, or in particular, increases with respect to the basic values. 35 to 38 indicate ranges for the signals from the two sensors 1, 2 or 26, 27 in which certain contaminants or impurities are often located. These ranges 35 to 38 are indicated by value ranges on the two axes 33 and 34. The range 35 relates, for example, to individual fibers made of plastic material. The range 36 relates, for example, to strips of plastic material and fiber bundles. The range 37 relates, for example, to human and animal hair. The range 38 relates, for example, to cloth fragments, greasy fiber bundles or larger or coarser contaminants overall.

Figure 6:
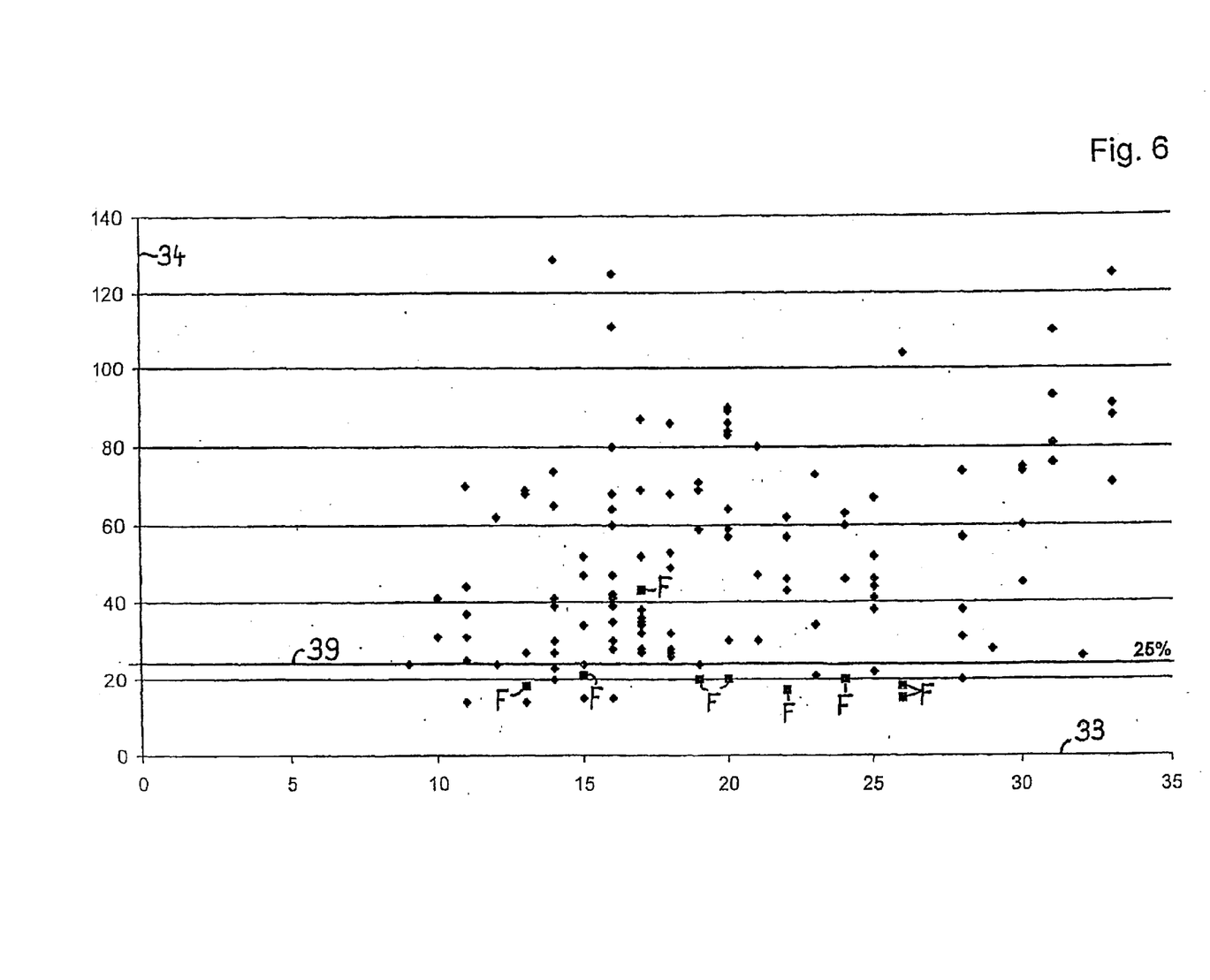

FIG. 6 shows a diagram with measured values for contaminants which are plotted over axes 33, 34, similar to FIG. 5, but here have a different graduation of the numerical values. Each data point in the diagram represents a specific impurity in one or more samples of strips or yarns that are measured by the sensors. The data points labeled F designate impurities that contain undesired foreign fibers. These labels are manually assigned by visually inspecting the strip or yarn samples to determine the type of impurity that is associated with each data point. Since impurities containing foreign fibers are of interest, the specific data points associated with those impurities are identified.

In the example of FIG. 6, it can be seen that most of the impurities containing foreign fibers are within the class of impurities in which the value on the axis 34 is below 25%. Accordingly, a limit value 39 can be selected which, based on the signals as shown on the axis 34, indicates this class of impurities.

Figure 7:
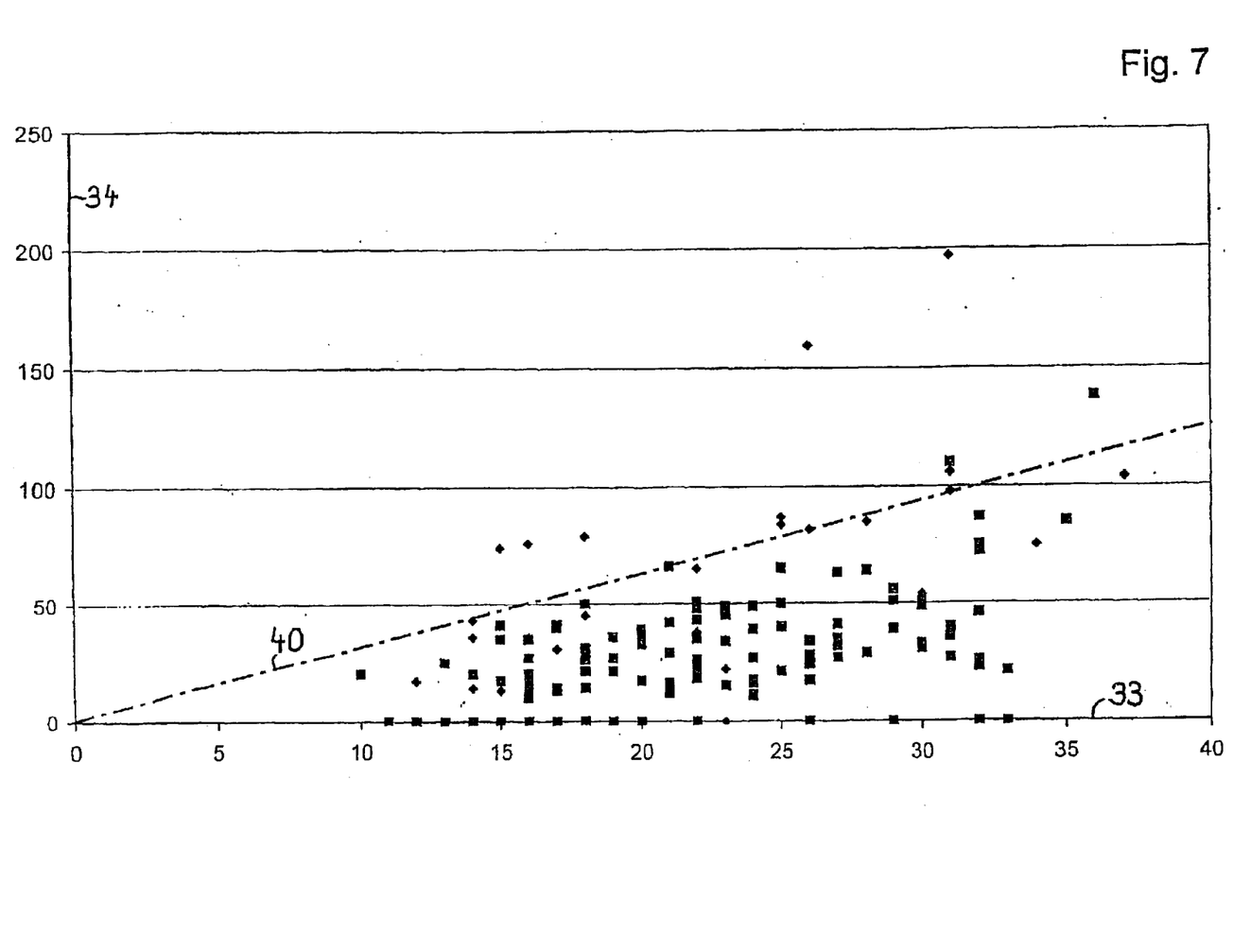

FIG. 7 shows a further diagram with measured values for contaminants for a different set of samples, which are plotted over axes 33, 34, similar to FIG. 5, but here having a different graduation of the numerical values. Undesired foreign fibers are designated by the rectangular symbols. For this example a limit 40 is selected which follows a function y=f(x), where x designates the values along the axis 33 and y the values along the axis 34. This limit 40 is empirically selected from visual inspection of the labeled data points, to indicate the class of impurities which contain most of the foreign fibers.

Figure 8:
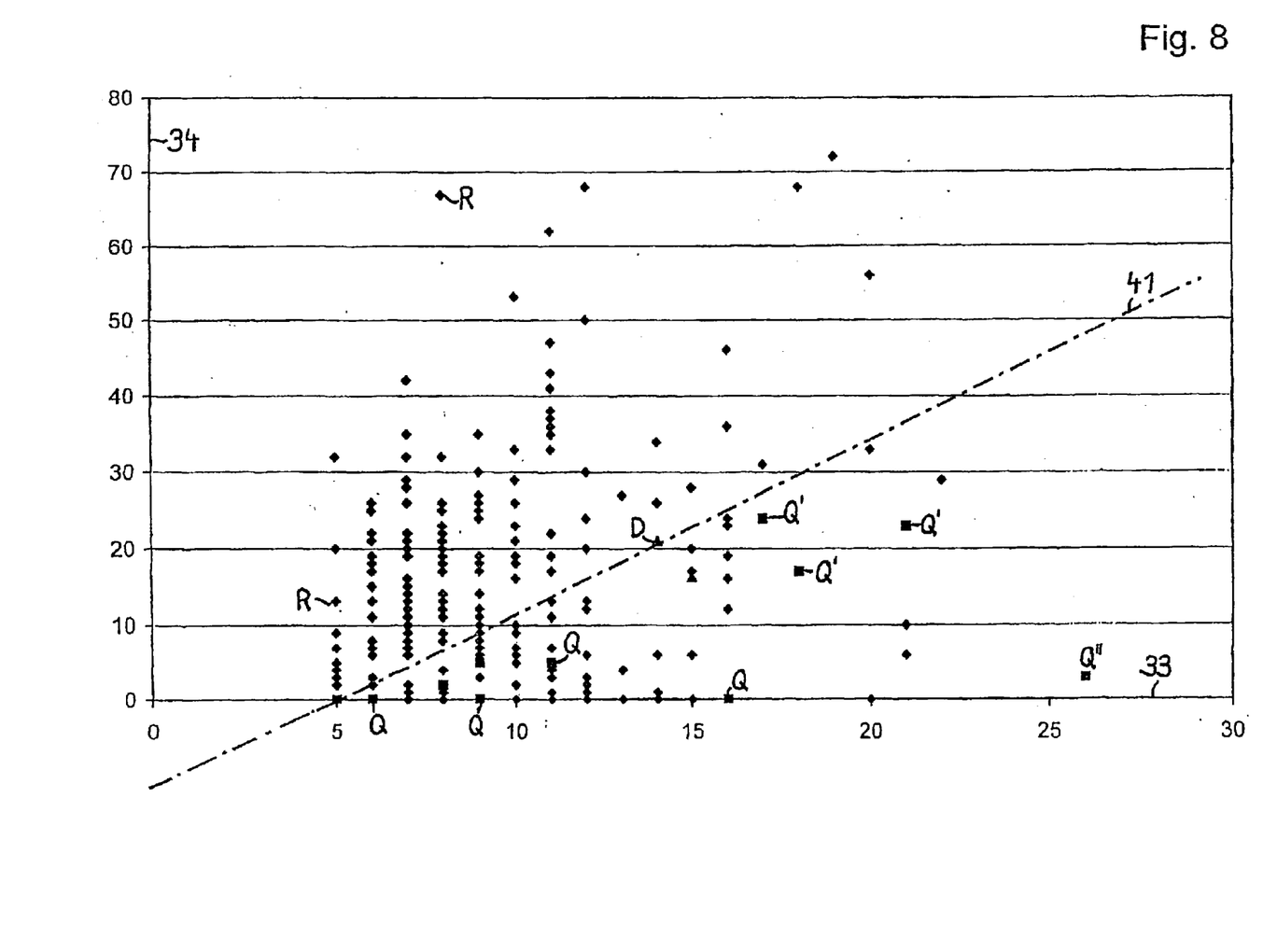

FIG. 8 shows a further diagram with measured values for contaminants in another set of samples, which are plotted over axes 33, 34, as in FIG. 5, but here having a different graduation of the numerical values. Contaminants of vegetable origin are designated by small rhombusses R, undesired fibers by small squares Q, residues of plastic strips by small triangles D, black hair by further squares Q' and residues of materials by small squares Q". Again, each of these labels are manually applied as a result of visual inspection of each impurity which generated a data point in the diagram. For this set of samples, a limit 41 is drawn which follows a function y=f(x)+x, where x designates the values along the axis 33 and y the value along the axis 34. The limit 41 indicates the class of impurities that contain the majority of each of the undesirable types of contaminants.

FIGS. 6 to 8 therefore show signals as can occur in the lines 4 and 5 but wherein here the course over time is not taken into account. In other words, all of the impurities are depicted on a common graph, independent of their relative locations in the samples. The circumstance where the values of the signals are vertically superimposed is due to the fact that only certain discrete values are shown for the values of the axis 33.

The mode of operation of the device and the method are as follows:

In the first sensor 1, 26 the strip or the yarn 3, 23 are exposed to a wave field 24, for example, light, for detecting a first parameter and a measurement is made as to how much light or wave energy can be detected again by reflection on the product. Here it is assumed that the reflection changes if impurities occur in the sensor 1, 26 and the signal, produced in the sensor 1, 26, differs from a basic value, determined by the base material. For example, the reflection changes if differently colored fibers or plastic parts suddenly occur in the yarn. The signal produced in the process can, in addition, be modified by a diameter or mass influence and could have a profile as is designated in FIG. 2 by 10, as known from U.S. Pat. No. 5,414,520. The first parameter is therefore the intensity of the reflected wave field or light, as is drawn, for example, in percent values along the axis 33 in FIGS. 5 to 8 proceeding from a basic value. To neutralize the influence of the mass of the strip or yarn in the signal in line 30 (FIG. 4), it is combined in the element 32 in a known manner with the signal from the line 31.

In the second sensor 2 a signal, offset by a time $\Delta t$, is generated, for example in a capacitively operating sensor 2, 27, which is proportional to the mass or to the diameter of the yarn 3, 23 in the detected portion. The signal resulting in this process (FIG. 2) could have a profile as is designated in FIG. 2 by 11. In each case a further parameter is therefore detected on the yarn in the form of an increase in diameter or mass, as is drawn, for example, in percent values also along the axis 34 in FIGS. 5 to 8 proceeding from a basic value.

The two signals are accordingly input via the lines 4, 5 or 30', 31, into the memory 7 of the processor 6 where they are stored. The time T during which they are stored is dependent on the evaluation criteria used. For example, the criteria could be the length or limit an impurity begins to be perceived to be disruptive. It is known, for example from the yarn test that very short faults are not disruptive if the increase in diameter owing to the fault is large, for example 100%. Therefore, limit values for the first and second signals variables are preset at a level that distinguish a disruptive impurity from a non-disruptive impurity that should simply be disregarded. Such limits are indicated in FIGS. 3 and 5 to 8 and they can be preset for the length and the increase in thickness or mass of the product owing to the impurity and also for the extent and duration of a reflection deviating from a basic value. This time T should accordingly also exceed at least the time which corresponds to the speed of the yarn multiplied by the length in accordance with the limit (line 21) for the length of the signal or the contaminant. This time T should preferably also be lengthened by the time $\Delta t$, so in a time segment 42 two signals are simultaneously present for a sufficiently long time.

In principle, only signals exceeding certain limits 20–21 or 22 (FIG. 3) should be subjected to the evaluation criteria, the limit 22 following a function making the two limits for the length and the thickness mutually dependent.

The following table 1, for example, can provide a simple evaluation criteria.

TABLE 1

|  | > Limit value | > Limit value |
| --- | --- | --- |
| Signal 1 | yes | no |
| Signal 2 | yes | no |

Here it can be determined, for example, that events causing both signals 1 and 2 to exceed the limit individually determined for each signal designate an instance of the sought impurity. This can be described in more detail with reference to FIGS. 5 to 8.

In the diagram of FIG. 5, ranges 35 to 38 can be detected for impurities or contaminants which are potentially undesirable. If this is the case then a limit, as shown by a line 43, is valid as an evaluation criterion. In this case only those contaminants are recognized and possibly eliminated which generate signals located below the line 43, i.e. exceed the basic value in accordance with axis 34 but not the limit in accordance with line 43. An increase of at least 5% for values of the axis 33 is also demanded. If, however, by way of example, only those contaminants which are located roughly in the region 38 are to be detected, then a line 44 could be provided as a limit instead of the line 43. Values for the reflection in the wave field are preferably drawn along the axis 33 and values for the increase in the capacity in an electrical field along the axis 34. If the reflection on the strip or yarn is detected, for example with light of a particular color, then distortions occur as contaminants of the same color will only emit an insufficient signal, so, for example, they are seemingly located in a region 45 instead of beyond the line 43 or 44. If, however, the second parameter is measured in an electrical field then the contaminant can nevertheless be easily detected by large values along the axis 34. Therefore insufficiencies of the one sensor can be compensated by the other sensor. For this purpose, it would then also be proper to displace the limits accordingly.

It can be seen in FIG. 6 that, with the limit value 39 in this case, 89% of the undesirable impurities are selected, but the class identified by the limit value 39 only simultaneously includes 12.8% of the harmless contaminants. This result is obtained by counting out the recorded events.

It can be seen in FIG. 7 that with the limit 40 in this case virtually all undesirable impurities can be selected with the identified class.

It can be seen in FIG. 8 that with the limit 41 in this case all undesirable impurities can be selected with the identified class. In addition, about 16% of harmless contaminants per se are simultaneously selected.

To distinguish between primarily vegetable and non-vegetable contaminants it is advantageous to detect a parameter in an electrical field. With capacitive detection it is namely the mass of the yarn or impurity which influences the signal and it does this to a much greater extent. This can be seen if it is imagined how small a change in mass affects the diameter. For example, with a cylindrical body an increase in the diameter of 10% produces an increase in the mass of 21%. However, this change in mass alone cannot be used to detect impurities as they also influence the surface of the strip or yarn. Therefore a further parameter is investigated and only the joint evaluation of both parameters produces a good result. If the desired classification between desired or tolerated and primarily undesirable impurities exists, the separating stage of a clearer for the strip or yarn can be controlled with the signal in output 9 (FIG. 1).

What is claimed is:

1. A method for detecting impurities in a longitudinally moving thread-like product made of textile fibers, comprising the following steps:
    detecting a first parameter on the product in a wave field, and generating a first signal indicating potentially present impurities;
    detecting a further parameter on the product in a field, and generating a second signal indicating potentially present impurities;
    allocating separate evaluation specifications to the first signal and second signal for the evaluation thereof; and
    identifying a class of impurities containing a specific type of impurity from the evaluated first and second signals.

2. The method according to claim 1, wherein the further parameter is selected from a group of variables comprising the mass and the diameter of a portion of the product.

3. The method according to claim 2, wherein the variables of said group are detected capacitively.

4. The method according to claim 1, wherein said first parameter is detected by measuring shadowing and the reflection of the wave field on the product to produce two signals, and combining said two signals to generate the first signal.

5. The method according to claim 1, wherein the first and second signals are stored over a time period, and wherein the two stored signals are evaluated, relative to an evaluation specification, and the type of impurity is determined from the evaluation.

6. The method according to claim 1, wherein said evaluation specifications are selected to provide a class of primarily vegetable impurities.

7. The method according to claim 6, wherein the evaluation specifications preset a limit for at least one of the two signals, to indicate a class containing primarily one type of impurity.

8. The method according to claim 1, wherein the wave field comprises visible light.

9. A device for detecting impurities in a longitudinally moving thread-like products, comprising a first sensor operating with a wave field, a second sensor operating with a field, a processor connected to the first sensor and the second sensor, a memory for time-limited storage of signals from the first sensor and the second sensor, and a software program for the processor that contains evaluation specifications for the first and second signals and generates a third signal from the first signal and the second signal that indicates a class of impurities in the product containing a specific type of impurity.

10. A device according to claim 9, wherein limits are preset for the signals as evaluation specifications.

11. A method for classifying impurities in a longitudinally moving thread-like product made of textile fibers, comprising the following steps:
    detecting a first parameter on the product in a wave field, and generating a first signal indicating potentially present impurities;
    detecting a further parameter on the product in a field, and generating a second signal indicating potentially present impurities;
    recording two-dimensional data points respectively corresponding to instances where at least one of said first and second signals indicates a potentially present impurity, where said dimensions respectively correspond to said parameters;
    labeling data points which are associated with at least one predetermined type of impurity; and
    establishing a limit which identifies a class of impurities in which impurities of said predetermined type are primarily contained.

12. The method of claim 11 wherein substantially all of the impurities of said predetermined type are contained in the class identified by said limit.

13. The method of claim 11, further including the step of controlling a yarn clearer in accordance with said limit to clear impurities that are contained within said class while leaving intact impurities outside of said class.

14. The method according to claim 11, wherein the further parameter is selected from a group of variables comprising the mass and the diameter of a portion of the product.

15. The method according to claim 14, wherein the variables of said group are detected capacitively.

16. The method according to claim 11, wherein said first parameter is detected by measuring shadowing and the reflection of the wave field on the product to produce two signals, and combining said two signals to generate the first signal.

17. The method according to claim 11, wherein the wave field comprises visible light.

18. The method of claim 1, wherein said evaluation specifications distinguish between plural different classes of impurities.

19. The device of claim 9, wherein said evaluation specifications distinguish between plural different classes of impurities.

20. The method of claim 11, wherein said limit distinguishes between at least two different classes of impurities.

* * * * *